(12) United States Patent
Pötter et al.

(10) Patent No.: US 9,580,732 B2
(45) Date of Patent: Feb. 28, 2017

(54) OXIDATION AND AMINATION OF PRIMARY ALCOHOLS

(75) Inventors: Markus Pötter, Shanghai (CN); Thomas Haas, Muenster (DE); Jan Christoph Pfeffer, Hanau (DE); Arne Skerra, Freising (DE); Wolfgang Kroutil, Graz (AT); Alexandra Lerchner, Neufahrn bei Freising (DE); Johann H. Sattler, Bad Aussee (AT); Steffen Schaffer, Herten (DE); Katharina Christin Tauber, Wolfsberg (AT)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/233,505

(22) PCT Filed: Jul. 17, 2012

(86) PCT No.: PCT/EP2012/063994
§ 371 (c)(1),
(2), (4) Date: Jan. 17, 2014

(87) PCT Pub. No.: WO2013/011018
PCT Pub. Date: Jan. 24, 2013

(65) Prior Publication Data
US 2014/0242646 A1    Aug. 28, 2014

(30) Foreign Application Priority Data

Jul. 20, 2011 (EP) .................................. 11174729
Aug. 5, 2011 (EP) .................................. 11006458
Jan. 9, 2012 (EP) .................................. 12150451

(51) Int. Cl.
*C12P 13/00* (2006.01)

(52) U.S. Cl.
CPC .................................. *C12P 13/001* (2013.01)

(58) Field of Classification Search
None
See application file for complete search history.

(56) References Cited

U.S. PATENT DOCUMENTS

| | | |
|---|---|---|
| 6,620,970 B2 | 9/2003 | Schiffer et al. |
| 6,639,108 B2 | 10/2003 | Schiffer et al. |
| 6,764,671 B2 | 7/2004 | Haas et al. |
| 6,861,540 B2 | 3/2005 | Herwig et al. |
| 6,878,836 B2 | 4/2005 | Haas et al. |
| 7,005,528 B2 | 2/2006 | Haas et al. |
| 7,030,052 B2 | 4/2006 | Stochniol et al. |
| 7,049,450 B2 | 5/2006 | Hofen et al. |
| 7,091,384 B2 | 8/2006 | Jaeger et al. |
| 7,157,610 B2 | 1/2007 | Hofen et al. |
| 7,507,862 B2 | 3/2009 | Stochniol et al. |
| 7,608,738 B2 | 10/2009 | Herwig et al. |
| 7,754,778 B2 | 7/2010 | Knott et al. |
| 7,879,938 B2 | 2/2011 | Häger et al. |
| 7,923,225 B2 | 4/2011 | Mueller et al. |
| 8,022,201 B2 | 9/2011 | Roos et al. |
| 8,168,841 B2 | 5/2012 | Herwig et al. |
| 8,216,813 B2 | 7/2012 | Thum et al. |
| 8,232,333 B2 | 7/2012 | Haeger et al. |
| 8,349,596 B2 | 1/2013 | Mueller et al. |
| 8,349,907 B2 | 1/2013 | Henning et al. |
| 8,372,595 B2 | 2/2013 | Schaffer et al. |
| 8,378,127 B2 | 2/2013 | Dingerdissen et al. |
| 8,399,658 B2 | 3/2013 | Hengstermann et al. |
| 8,404,470 B2 | 3/2013 | Thum et al. |
| 8,445,720 B2 | 5/2013 | Hannen et al. |
| 8,486,677 B2 | 7/2013 | Thum et al. |
| 8,604,227 B2 | 12/2013 | Petrat et al. |
| 8,796,000 B2 | 8/2014 | Thum et al. |
| 8,871,862 B2 | 10/2014 | Pawlik et al. |
| 9,000,223 B2 | 4/2015 | Micoine et al. |
| 2002/0087036 A1 | 7/2002 | Haas et al. |
| 2003/0212298 A1 | 11/2003 | Brasse et al. |
| 2005/0192441 A1 * | 9/2005 | Hu .................. C07C 269/06 548/200 |
| 2009/0148899 A1 | 6/2009 | Kawano et al. |
| 2010/0068773 A1 | 3/2010 | Marx et al. |
| 2010/0167360 A1 | 7/2010 | Thum et al. |
| 2010/0190224 A1 | 7/2010 | Poetter et al. |

(Continued)

FOREIGN PATENT DOCUMENTS

| | | | |
|---|---|---|---|
| DE | 10 2007 060705 A1 | 6/2009 | |
| EP | 2 022 852 A1 | 2/2009 | |
| NL | WO 2011031146 A2 * | 3/2011 | ............... C12P 7/44 |
| WO | WO 2010/085731 A2 | 7/2010 | |
| WO | WO 2010/085731 A3 | 7/2010 | |
| WO | WO 2012/113475 A1 | 8/2012 | |
| WO | WO 2012/171666 A1 | 12/2012 | |
| WO | WO 2013/011018 A1 | 1/2013 | |
| WO | WO 2013/020839 A1 | 2/2013 | |
| WO | WO 2013/135650 A1 | 9/2013 | |

OTHER PUBLICATIONS

Karabec M et al. Structural insights into substrate specificity and solvent tolerance in alcohol dehydrogenase ADH-'A' from Rhodococcus ruber DSM 44541. 2010. Chem. Commun. 46. 6314-6316.*

(Continued)

*Primary Examiner* — Paul Holland
(74) *Attorney, Agent, or Firm* — Oblon, McClelland, Maier & Neustadt, L.L.P.

(57) ABSTRACT

A method including the steps a) providing a primary alcohol of the formula HO—$(CH_2)_x$—$R^1$, where $R^1$ is —OH, —SH, —$NH_2$ or —$COOR^2$; x is at least 3; and $R^2$ is H, alkyl or aryl, b) oxidizing the primary alcohol by contacting it with an $NAD(P)^+$-dependent alcohol dehydrogenase, and c) contacting the oxidation product of step a) with a transaminase, where the $NAD(P)^+$-alcohol dehydrogenase and/or the transaminase is a recombinant or isolated enzyme. A whole cell catalyst for carrying out the method. The use of such a whole cell catalyst for oxidizing a primary alcohol.

19 Claims, 1 Drawing Sheet

(56) References Cited

U.S. PATENT DOCUMENTS

| | | |
|---|---|---|
| 2010/0248325 A1 | 9/2010 | Eckstein et al. |
| 2010/0261237 A1 | 10/2010 | Verseck et al. |
| 2010/0266518 A1 | 10/2010 | Springer et al. |
| 2010/0291644 A1 | 11/2010 | Marx et al. |
| 2010/0324257 A1 | 12/2010 | Karau et al. |
| 2011/0014669 A1 | 1/2011 | Madden et al. |
| 2011/0039313 A1 | 2/2011 | Verseck et al. |
| 2011/0118433 A1 | 5/2011 | Pötter et al. |
| 2011/0118504 A1 | 5/2011 | Haas et al. |
| 2011/0171702 A1 | 7/2011 | Reinecke et al. |
| 2011/0189742 A1 | 8/2011 | Haas et al. |
| 2011/0251399 A1 | 10/2011 | Dingerdissen et al. |
| 2011/0257429 A1 | 10/2011 | Schraven et al. |
| 2012/0034665 A1 | 2/2012 | Haas et al. |
| 2012/0041216 A1 | 2/2012 | Sieber et al. |
| 2012/0245375 A1 | 9/2012 | Hannen et al. |
| 2012/0264182 A1 | 10/2012 | Reinecke et al. |
| 2012/0264877 A1 | 10/2012 | Häger et al. |
| 2012/0315366 A1 | 12/2012 | Zehnacker et al. |
| 2013/0035403 A1 | 2/2013 | Schaffer et al. |
| 2013/0052700 A1 | 2/2013 | Poetter et al. |
| 2013/0092232 A1 | 4/2013 | Pawlik et al. |
| 2013/0092233 A1 | 4/2013 | Pawlik et al. |
| 2013/0130319 A1 | 5/2013 | Schaffer et al. |
| 2013/0164797 A1 | 6/2013 | Gielen et al. |
| 2013/0165672 A1 | 6/2013 | Klasovsky et al. |
| 2013/0165685 A1 | 6/2013 | Hannen et al. |
| 2013/0171388 A1 | 7/2013 | Pawlik et al. |
| 2013/0183725 A1 | 7/2013 | Poetter et al. |
| 2013/0207050 A1 | 8/2013 | Hermasch et al. |
| 2013/0240799 A1 | 9/2013 | Haeger et al. |
| 2013/0245276 A1 | 9/2013 | Klasovsky et al. |
| 2013/0299750 A1 | 11/2013 | Hermasch et al. |
| 2013/0331580 A1 | 12/2013 | Klasovsky et al. |
| 2014/0039071 A1 | 2/2014 | Thum et al. |
| 2014/0039210 A1 | 2/2014 | Erhardt et al. |
| 2014/0039223 A1 | 2/2014 | Klasovsky et al. |
| 2014/0054224 A1 | 2/2014 | Erhardt et al. |
| 2014/0141478 A1 | 5/2014 | Schaffer et al. |
| 2014/0178948 A1 | 6/2014 | Schaffer et al. |
| 2014/0199736 A1 | 7/2014 | Köhler et al. |

OTHER PUBLICATIONS

Stark D et al. Extractive Bioconversion of 2-Phenyethanol from L-Phenylalanie by *Saccharomyces cerevisiae*. 2002. Biotechnology Progress. 18. 514-523.*

U.S. Appl. No. 14/363,178, filed Jun. 5, 2014, Haas, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/380,483, filed Aug. 22, 2014, Schiemann, et al.
U.S. Appl. No. 14/435,339, filed Apr. 13, 2015, Engel, et al.
U.S. Appl. No. 14/419,580, filed Feb. 4, 2015, Erhardt, et al.
U.S. Appl. No. 14/425,180, filed Mar. 2, 2015, Ortelt, et al.
International Search Report issued Sep. 19, 2012 in PCT/EP2012/063994.
Hyungdon Yun, et al., "Simultaneous synthesis of enantiomerically pure (R)-1-phenylethanol and (R)-α-methylbenzylamine from racemic α-methylbenzylamine using ω-transaminase/alcohol dehydrogenase/glucose dehydrogenase coupling reaction" Biotechnology Letters, vol. 25, No. 10, XP002420353, May 1, 2003 pp. 809-814.
Akinobu Matsuyama, et al., "Practical Application of Recombinant Whole-Cell Biocatalysts for the Manufacturing of Pharmaceutical Intermediates Such as Chiral Alcohols" Organic Process Research and Development, vol. 6, No. 4, XP002344756, Jan. 1, 2001, pp. 558-561.
Andrea Weckbecker, et al., "Improved synthesis of chiral alcohols with *Escherichia coli* cells co-expressing pyridine nucleotide transhydrogenase, NADP$^+$-dependent formate dehydrogenase" Biotechnology Letters, vol. 26, XP002344979, Nov. 1, 2004, pp. 1739-1744.
Hyungdon Yun, et al., "Asymmetric Synthesis of (S)-α-Methylbenzylamine by Recombinant *Escherichia coli* Co-Expressing Omega-Transaminase and Acetolactate Synthase" Bioscience Biotechnology and Biochemistry, vol. 72, No. 11, XP002665945, Nov. 2008, pp. 3030-3033.
Dominik Kozelewski, et al., "Synthesis of Optically Active Amines Employing Recombinant ω-Transaminases in *E. Coli* Cells" ChemCatChem, vol. 2, No. 1, XP002665946, 2010, pp. 73-77.
U.S. Appl. No. 14/126,607, filed Dec. 16, 2013, Haas, et al.
U.S. Appl. No. 14/237,121, filed Feb. 4, 2014, Haas, et al.
U.S. Appl. No. 14/238,576, filed Feb. 12, 2014, Schaffer, et al.
U.S. Appl. No. 14/238,591, filed Feb. 12, 2014, Schaffer, et al.
U.S. Appl. No. 14/384,301, filed Sep. 10, 2014, Schaffer, et al.
U.S. Appl. No. 14/390,133, filed Oct. 2, 2014, Hennemann, et al.
U.S. Appl. No. 14/395,666, filed Oct. 20, 2014, Haas, et al.
U.S. Appl. No. 14/405,050, filed Dec. 2, 2014, Haas, et al.
U.S. Appl. No. 14/400,379, filed Nov. 11, 2014, Haas, et al.
U.S. Appl. No. 14/763,378, filed Jul. 24, 2015, Haas, et al.
U.S. Appl. No. 14/649,414, filed, Jun. 3, 2015, Schaffer et al.

* cited by examiner

| | | |
|---|---|---|
| TACV_co | VVAARWLEEKILE--IGADKVAAFVGEPIQGAGGVIVPPA-TYWPEIERICRKYDVLLVA | 258 |
| Q1GD43_3FCR_ | AHCVAELEALIER--EGADTIAAFIGEPILGTGGIVPPPA-GYWEAIQTVLNKHDILLVA | 258 |
| Q987B2_3GJU_ | QHCADKLEEMLLA--EGPETIAAFIGEPILGTGGIVPPPA-GYWEKIQAVLKKYDVLLVA | 259 |
| Q3IWE9_3I5T_ | DDLVQEFEDRIES--LGPDTIAAFLAEPILASGGVIIPPA-GYHARFKAICEKHDILYIS | 259 |
| 1.5.020 | AELANELERIVAL--HDASTIAAVIVEPVAGSTGVILPPK-GYLQKLREICTKHGILLIF | 254 |
| 1.5.021 | AELANELERIVAL--HDASTIAAVIVEPVAGSTGVILPPK-GYLQKLREICTKHGILLIF | 254 |
| Ade | AHLADELERIIAL--HDASTIAAVIVEPMAGSTGVLVPPK-GYLEKLREITARHGILLIF | 252 |
| TA_R.eu | AHLADELERIVAL--HDPSTIAAVIVEPLAGSAGVLVPPV-GYLDKLREITTKHGILLIF | 254 |
| TA5_Pao132 | VELANELLKLIEL--HDASNIAAVIVEPMSGSAGVLVPPV-GYLQRLREICDQHNILLIF | 270 |
| P28269_3A8U_ | IALADELLKLIEL--HDASNIAAVFVEPLAGSAGVLVPPE-GYLKRNREICNQHNILLVF | 258 |
| P0A4X6_3BV0_ | PAYSAAFEAQLAQ--HAGELAAVVVEPVVQGAGGMRFHDP-RYLHDLRDICRRYEVLLIF | 253 |
| P12995_1S0A_ | ERDMVGFARLMAA--HRHEIAAVIIEPIVQGAGGMRMYHP-EWLKRIRKICDREGILLIA | 244 |
| P53555_3DOD_ | DQCLRELAQLLEE--HHEEIAALSIESMVQGASGMIVMPE-GYLAGVRELCTTYDVLMIV | 250 |
| 1.5.017 | ---ANEIDRIMTW--ELSETIAGVIMEPIITGGGILMPPD-GYMKKVEDICRRHGALLIC | 253 |
| Aci | LLSVKYTRRMIEN--YGPEQVAAVITEVSQGAG-SAMPPY-EYIPQFRKMTKELGVLWIN | 268 |
| Bme | LLSVKYTRRMIEN--YGPEQVAAVITEVSQGAG-SAMPPY-EYIPQIRKMTKELGVLWIN | 268 |
| TA_Aci_mut | LLSVKYTRRMIEN--YGPEQVAAVITEVSQGVG-STMPPY-EYVPQIRKMTKELGVLWIS | 268 |
| pCR05 | -KYASDVHDLIQF--GTSGQVAGFIGESIQVGGIVELAP-GYLPAAYDIVRKAGGVCIA | 294 |
| P16932_1ZOD_ | LAELDYAFDLIDR--QSSGNLAAFIAEPILSSGGIIELPD-GYMAALKRKCEARGMLLIL | 242 |

OXIDATION AND AMINATION OF PRIMARY ALCOHOLS

The present invention relates to a method comprising the steps
a) providing a primary alcohol of the formula

HO—(CH$_2$)$_x$—R$^1$, wherein R$^1$ is selected from the group consisting of —OH, —SH, —NH$_2$ and —COOR$^2$, x is at least 3 and R$^2$ is selected from the group consisting of H, alkyl and aryl,
b) oxidizing the primary alcohol by contacting it with an NAD(P)$^+$-dependent alcohol dehydrogenase, and
c) contacting the oxidation product of step a) with a transaminase,
wherein the NAD(P)$^+$-dependent alcohol dehydrogenase and/or the transaminase is a recombinant or isolated enzyme,
a whole cell catalyst for carrying out the method, and the use of such a whole cell catalyst for oxidizing a primary alcohol.

Polyamides are a class of polymers which are characterized by repeating amide groups. The expression "polyamides", in contrast to the chemically related proteins, usually relates to synthetic, commercially available thermoplastics. Polyamides are derived from primary amines or from secondary amines, which are customarily obtained on cracking of hydrocarbons. However, derivatives, more precisely aminocarboxylic acids, lactams and diamines, can also be used for polymer production. In addition, short-chain gaseous alkanes are of interest as reactants, which can be obtained starting from renewable raw materials using methods of biotechnology.

Many polyamides in great demand commercially are produced starting from lactams. For example, "polyamide 6" can be obtained by polymerizing ε-caprolactam and "polyamide 12" by polymerizing laurolactam. Further commercially interesting products comprise copolymers of lactam, for example copolymers of ε-caprolactam and laurolactam.

The conventional chemical industry generation of amines is dependent on supply with fossil raw materials, is inefficient and in the process large amounts of undesirable by-products occur, in some step of the synthesis up to 80%. One example of such a process is the production of laurolactam which is conventionally obtained by trimerizing butadiene. The trimerization product cyclododecatriene is hydrogenated and the resultant cyclododecane is oxidized to cyclododecanone which is then reacted with hydroxylamine to form cyclododecanonoxin, which is finally converted via a Beckmann rearrangement to laurolactam.

Mindful of these disadvantages, methods have been developed in order to obtain amines using biocatalysts, proceeding from renewable raw materials. PCT/EP 2008/067447 describes a biological system for producing chemically related products, more precisely ω-aminocarboxylic acids, using a cell which has a number of suitable enzymatic activities and is able to convert carboxylic acids to the corresponding ω-aminocarboxylic acid. A known disadvantage of the AlkBGT-oxidase system from *Pseudomonas putida* GPO1 used in this method is, however, that it is not able to perform a selective oxidation of aliphatic alkanes to primary alcohols. Rather, a multiplicity of oxidation products occur; in particular the fraction of more highly oxidized products such as the corresponding aldehyde, ketone or the corresponding carboxylic acid increases with increasing reaction time (C. Grant, J. M. Woodley and F. Baganz (2011), *Enzyme and Microbial Technology* 48, 480-486), which correspondingly reduces the yield of the desired amine.

Against this background, the object of the invention is to provide an improved method for oxidizing alcohols using biocatalysts. A further object is to improve the method in such a manner that the yield is increased and/or the concentration of by-products is decreased. Finally, there is a need for a method that permits the production of polyamides or reactants for production thereof based on renewable raw materials.

These and other objects are achieved by the subject matter of the present application and in particular, also, by the subject matter of the accompanying independent claims, wherein embodiments result from the subclaims.

According to the invention, the object is achieved in a first aspect by a method comprising the steps
a) providing a primary alcohol of the formula

HO—(CH$_2$)$_x$—R$^1$, wherein R$^1$ is selected from the group consisting of —OH, —SH, —NH$_2$ and —COOR$^2$, x is at least 3 and R$^2$ is selected from the group consisting of H, alkyl and aryl,
b) oxidizing the primary alcohol by contacting it with an NAD(P)$^+$-dependent alcohol dehydrogenase, and
c) contacting the oxidation product of step a) with a transaminase,
wherein the NAD(P)$^+$-dependent alcohol dehydrogenase and/or the transaminase is a recombinant or isolated enzyme.

In a first embodiment of the first aspect, step a) proceeds by hydroxylating an alkane of the formula

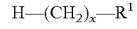
H—(CH$_2$)$_x$—R$^1$ by a monooxygenase which is preferably a recombinant or isolated monooxygenase.

In a second embodiment of the first aspect, which is also an embodiment of the first embodiment, the NAD(P)$^+$-dependent alcohol dehydrogenase is an NAD(P)$^+$-dependent alcohol dehydrogenase having at least one zinc atom as cofactor.

In a third embodiment of the first aspect, which is an embodiment of the second embodiment, the alcohol dehydrogenase is an alcohol dehydrogenase from *Bacillus stearothermophilus* (database code P42328) or a variant thereof.

In a fourth embodiment of the first aspect, which is an embodiment of the first to third embodiments, the monooxygenase is selected from the group consisting of AlkBGT from *Pseudomonas putida*, cytochrome P450 from *Candida tropicalis*, or from *Cicer arietinum*.

In a fifth embodiment of the first aspect, which is also an embodiment of the first to fourth embodiments, the transaminase is selected from the group of transaminases and variants thereof which are characterized in that, at the position of the amino acid sequence which corresponds to Val224 from the transaminase of *Chromobacterium violaceum* ATCC 12472 (database code NP_901695), it has an amino acid selected from the group consisting of isoleucine, valine, phenylalanine, methionine and leucine, and, at the position of the amino acid sequence which corresponds to Gly230 from the transaminase of *Chromobacterium violaceum* ATCC 12472 (database code NP_901695), has an amino acid other than threonine and preferably an amino acid from the group consisting of serine, cystein, glycine and alanine.

In a sixth embodiment of the first aspect, which is also an embodiment of the first to fifth embodiments, step b) and/or step c) is carried out in the presence of an isolated or recombinant alanine dehydrogenase and an inorganic nitrogen source.

In a seventh embodiment of the first aspect, which is also an embodiment of the first to sixth embodiments, at least one enzyme of the group consisting of $NAD(P)^+$-dependent alcohol dehydrogenase, transaminase, monooxygenase and alanine dehydrogenase is recombinant and is provided in the form of a whole cell catalyst which comprises the corresponding enzyme.

In an eighth embodiment of the first aspect, which is an embodiment of the seventh embodiment, all enzymes are provided in the form of one or more as a whole cell catalyst wherein, preferably, a whole cell catalyst comprises all necessary enzymes.

In a ninth embodiment of the first aspect, which is also an embodiment of the first to eighth embodiments, in the case of step b), preferably in the case of steps b) and c), an organic cosolvent is present which has a log P of greater than −1.38, preferably 0 to 1.2.

In a tenth embodiment of the first aspect, which is an embodiment of the ninth embodiment, the cosolvent is selected from the group consisting of unsaturated fatty acids, preferably oleic acid.

In an eleventh embodiment of the first aspect, which is a preferred embodiment of the ninth embodiment, the cosolvent is a compound of the formula $R^3$—O—$(CH_2)_x$—O—$R^4$, wherein $R^3$ and $R^4$ are each, and independently of one another, selected from the group consisting of methyl, ethyl, propyl and butyl, and x is 1 to 4, wherein particularly preferably $R^3$ and $R^4$ are each methyl and x is 2.

In a twelfth embodiment of the first aspect, which is a preferred embodiment of the ninth embodiment, the cosolvent is selected from the group consisting of dialkyl ethers and is preferably dimethyl ether.

According to the invention the object is achieved in a second aspect by a whole cell catalyst comprising an $NAD(P)^+$-dependent alcohol dehydrogenase, preferably having at least one zinc atom as cofactor, a transaminase, optionally a monooxygenase, and optionally an alanine dehydrogenase, wherein the enzymes are recombinant enzymes.

According to the invention, the object is achieved in a third aspect by the use of a whole cell catalyst as claimed in the second aspect of the present invention for oxidizing and aminating a primary alcohol of the formula HO—$(CH_2)_x$—$R^1$, wherein $R^1$ is selected from the group consisting of —OH, —SH, —$NH_2$ and —$COOR^2$, x is at least 3, and $R^2$ is selected from the group consisting of H, alkyl and aryl.

In a first embodiment of the third aspect, which is an embodiment of the first embodiment, the use further comprises the presence of an organic solvent which has a log P of greater than −1.38, preferably 0 to 1.2, and is preferably dimethyl ether.

In a second embodiment of the third aspect, which is an embodiment of the second embodiment, the cosolvent is selected form the group consisting of the unsaturated fatty acids, and is preferably oleic acid.

Further embodiments of the second and third aspects comprise all embodiments of the first aspect of the present invention.

The inventors of the present invention have surprisingly found that there is a group of alcohol hydrogenases which can be used to effect the oxidation of primary alcohols, with the formation of lower amounts of by-products.

The inventors have further surprisingly found that a cascade of enzymatic activities exists by which alcohols can be aminated without significant formation of by-products, using biocatalysts, wherein no reduction equivalents need to be added or removed.

The inventors have further surprisingly found a method by which polyamides surprisingly can be produced, using a whole cell catalyst, and proceeding from renewable raw materials.

The inventors of the present invention have further surprisingly found that the amination of primary alcohols after a preceding oxidation can be carried out particularly advantageously by a group of transaminases characterized by certain sequence properties.

The inventors of the present invention have surprisingly found that, in a system for oxidizing and aminating primary alcohols comprising an alcohol dehydrogenase, a transaminase and an alanine dehydrogenase, the use of an alcohol dehydrogenase other than one of AlkJ type, in particular the use of an $NAD(P)^+$-dependent alcohol dehydrogenase, is advantageous with regard to the yield of the method, particularly in the case of implementation using a whole cell catalyst.

The method according to the invention can be applied to a great number of industrially relevant alcohols. In a preferred embodiment, this concerns a ω-hydroxycarboxylic acid or an ester, preferably methyl ester, thereof, which is oxidized and aminated to give a ω-aminocarboxylic acid. In a further embodiment, this is a diol which is oxidized and aminated to form a diamine. In a further preferred embodiment, the primary alcohol is a hydroxyalkylamine. The length of the carbon chain here is variable and x is at least 3. Preferably, the carbon chain has more than three carbon atoms, i.e. x=4, 5, 6, 7, 8, 9, 10, 11, 12, 13, 14, 15, 16, 17, 18, 19, 20 or more. Exemplary compounds comprise ω-hydroxylauric acid, ω-hydroxylauric acid methyl ester, and alkanediols, in particular 1,8-octanediol and 1,10-decanediol.

In a particularly preferred embodiment, $R^1$ is selected from the group consisting of —OH and —$COOR^2$, x is at least 11, and $R^2$ is selected from the group consisting of H, methyl, ethyl and propyl. In a most preferred embodiment, the primary alcohol is a ω-hydroxy fatty acid methyl ester.

According to the invention, in step b) of the method, $NAD(P)^+$-dependent alcohol dehydrogenases are used for oxidizing the primary alcohol. In this case it can be, as with all enzymatically active polypeptides used according to the invention, cells comprising enzymatically active polypeptides, or lysates thereof, or preparations of the polypeptides in all purification stages, from the crude lysate to the pure polypeptide. Those skilled in the art in this field know numerous methods with which enzymatically active polypeptides can be overexpressed in suitable cells and purified or isolated. Thus, for expression of the polypeptides, all expression systems available to those skilled in the art can be used. For purification, chromatographic methods come into consideration, for example the affinity-chromatographic purification of a Tag-provided recombinant protein, using an immobilized ligand, for example a nickel ion in the case of a histidine Tag, immobilized glutathione in the case of a glutathione-S-transferase that is fused to the target protein, or immobilized maltose, in the case of a Tag comprising maltose-binding protein.

The purified enzymatically active polypeptides can be used either in soluble form or immobilized. Those skilled in the art know suitable methods with which polypeptides can be immobilized covalently or non-covalently to organic or inorganic solid phases, for example by sulfhydryl coupling chemistry (e.g. kits from Pierce).

In a preferred embodiment, the whole cell catalyst, or the cell used as an expression system is a prokaryotic cell, preferably a bacterial cell. In a further preferred embodiment, it is a mammalian cell. In a further preferred embodiment, it is a lower eukaryotic cell, preferably a yeast cell. Exemplary prokaryotic cells comprise *Escherichia*, particularly *Escherichia coli*, and strains of the genus *Pseudomonas* and *Corynebacterium*. Exemplary lower eukaryotic cells comprise the genera *Saccharomyces, Candida, Pichia, Yarrowia, Schizosaccharomyces*, particularly the strains *Candida tropicalis, Schizosaccharomyces pombe, Pichia pastoris, Yarrowia lipolytica* and *Saccharomyces cerivisiae*.

In a particularly preferred embodiment, the alcohol dehydrogenase is a zinc-containing NAD(P)$^+$-dependent alcohol dehydrogenase, i.e. the catalytically active enzyme comprises at least one zinc atom as cofactor which is bound covalently to the polypeptide by a characteristic sequence motif comprising cysteine residues. In a particularly preferred embodiment, the alcohol dehydrogenase is the alcohol dehydrogenase of *Bacillus stearothermophilus* (database code P42328) or a variant thereof.

The teaching of the present invention can be carried out not only using the exact amino acid sequences or nucleic acid sequences of the biological macromolecules described herein, but also using variants of such macromolecules which can be obtained by deletion, addition or substitution of one or more than one amino acids or nucleic acids. In a preferred embodiment, the expression "variant" means a nucleic acid sequence or amino acid sequence, hereinafter used synonymously and exchangeably with the expression "homolog", as used herein, another nucleic acid or amino acid sequence which, with respect to the corresponding original wild type nucleic acid or amino acid sequence, has a homology, here used synonymously with identity, of 70, 75, 80, 85, 90, 92, 94, 96, 98, 99% or more, wherein, preferably, other than those amino acids forming the catalytically active center or amino acids essential for the structure or folding, are deleted or substituted, or the latter are merely conservatively substituted, for example a glutamate instead of an aspartate, or a leucine instead of a valine. The prior art describes algorithms which can be used in order to calculate the extent of homology of two sequences, e.g. Arthur Lesk (2008), Introduction to bioinformatics, 3$^{rd}$ edition. In a further preferred embodiment of the present invention, the variant has an amino acid sequence or nucleic acid sequence, preferably in addition to the abovementioned sequence homology, substantially the same enzymatic activity of the wild type molecule, or of the original molecule. For example, a variant of a polypeptide that is enzymatically active as a protease has the same or substantially the same proteolytic activity as the polypeptide enzyme, i.e. the ability to catalyze the hydrolysis of a peptide bond. In a particular embodiment, the expression "substantially the same enzymatic activity" means an activity with regard to the substrates of the wild type polypeptide, which is markedly above the background activity and/or differs by less than 3, more preferably 2, still more preferably one, order of magnitude from the $K_M$ and/or $k_{cat}$ values which the wild type polypeptide has with respect to the same substrates. In a further preferred embodiment, the expression "variant" of a nucleic acid sequence or amino acid sequence comprises at least one active part/or fragment of the nucleic acid or amino acid sequence. In a further preferred embodiment, the expression "active part", as used herein, means an amino acid sequence, or a nucleic acid sequence, which is less than the whole length of the amino acid sequence, or encodes a lower length than the full length of the amino acid sequence, wherein the amino acid sequence or the encoded amino acid sequence having a shorter length than the wild type amino acid sequence has substantially the same enzymatic activity as the wild type polypeptide or a variant thereof, for example as alcohol dehydrogenase, monooxygenase, or transaminase. In a particular embodiment, the expression "variant" of a nucleic acid is a nucleic acid, the complementary strand of which binds to the wild type nucleic acid, preferably under stringent conditions. The stringency of the hybridization reaction is readily determinable by those skilled in the art, and generally depends on the length of the probe, on the temperatures during washing, and the salt concentration. Generally, longer probes require higher temperatures for the hybridization, whereas shorter probes manage with low temperatures. Whether hybridization takes place depends generally on the ability of the denatured DNA to anneal to complementary strands which are present in their surroundings, more precisely beneath the melting temperature. The stringency of hybridization reaction and corresponding conditions are described in more detail in Ausubel et al. 1995. In a preferred embodiment, the expression "variant" of a nucleic acid, as used therein, is a desired nucleic acid sequence which encodes the same amino acid sequence as the original nucleic acid, or encodes a variant of this amino acid sequence in the context of generic degeneracy of the genetic code.

Alcohol dehydrogenases, for decades, have been a highly regarded and biotechnologically highly relevant class of enzymes in biochemistry in connection with brewing fermentation processes, which class of enzymes comprises various groups of isoforms. Thus, membrane-bound, flavin-dependent alcohol dehydrogenases of the *Pseudomonas putida* GPO1 AlkJ type exist which use flavor cofactors instead of NAD(P)$^+$. A further group comprises iron-containing, oxygen-sensitive alcohol dehydrogenases which are found in bacteria and in inactive form in yeast. Another group comprises NAD(P)$^+$-dependent alcohol dehydrogenases, including zinc-containing alcohol dehydrogenases, in which the active center has a cysteine-coordinated zinc atom, which fixes the alcohol substrate. In a preferred embodiment, under the expression "alcohol dehydrogenase", as used herein, it is understood to mean an enzyme which oxidizes an aldehyde or ketone to the corresponding primary or secondary alcohol. Preferably, the alcohol dehydrogenase in the method according to the invention is an NAD(P)$^+$-dependent alcohol dehydrogenase, i.e. an alcohol dehydrogenase which uses NAD(P)$^+$ as a cofactor for oxidation of the alcohol or NAD(P)H for reduction of the corresponding aldehyde or ketone. In the most preferred embodiment, the alcohol dehydrogenase is an NAD(P)$^+$-dependent, zinc-containing alcohol dehydrogenase. In a preferred embodiment, the expression "NAD(P)$^+$-dependent alcohol dehydrogenase", as used herein, designates an alcohol dehydrogenase which is NAD$^+$- and/or NADP$^+$-dependent.

According to the invention, in step c), a transaminase is used. In a preferred embodiment, the expression "transaminase", as used herein, is taken to mean an enzyme which catalyzes the transfer of α-amino groups from a donor, preferably an amino acid, to an acceptor molecule, preferably a α-ketocarboxylic acid. In a preferred embodiment, the transaminase is selected from the group of transaminases and variants thereof which are characterized in that, at the position of the amino acid sequence which corresponds to Val224 from the transaminase of *Chromobacterium viola-* ceum ATCC 12472 (database code NP_901695), it has an amino acid selected from the group consisting of isoleucine, valine, phenylalanine, methionine and leucine, and, at the position of the amino acid sequence which corresponds to Gly230 from the transaminase of *Chromobacterium violaceum* ATCC 12472 (database code NP_901695), has an amino acid other than threonine and preferably an amino acid from the group consisting of serine, cystein, glycine and alanine. In a particularly preferred embodiment, the transaminase is selected from the group which consists of the ω-transaminase from *Chromobacterium violaceum* DSM30191, transaminases from *Pseudomonas putida* W619, from *Pseudomonas aeruginosa* PA01, *Streptomyces coelicolor* A3(2) and *Streptomyces avermitilis* MA 4680.

In a preferred embodiment, the expression "position which corresponds to the position λ of the amino acid sequence from the transaminase of *Chromobacterium violaceum* ATCC 12472", as used herein, means that the corresponding position, in an alignment of the molecule under study, appears homologous to the position X of the amino acid sequence of the transaminase of *Chromobacterium violaceum* ATCC 12472. Those skilled in the art know numerous software packages and algorithms with which an alignment of amino acid sequences can be made. Exemplary software packages methods comprise the package ClustalW provided by EMBL (Larkin et al., 2007; Goujon et al. 2010), or are listed and described in Arthur M. Lesk (2008), Introduction to Bioinformatics, 3rd edition.

The enzymes used according to the invention are preferably recombinant enzymes. In a preferred embodiment, the expression "recombinant", as used herein, is taken to mean that the corresponding nucleic acid molecule does not occur in nature, and/or it was produced using methods of genetic engineering. In a preferred embodiment, a recombinant protein is mentioned when the corresponding polypeptide is encoded by a recombinant nucleic acid. In a preferred embodiment, a recombinant cell, as used herein, is taken to mean a cell which has at least one recombinant nucleic acid or a recombinant polypeptide. Suitable methods, for example those described in Sambrook et al., 1989, are known to those skilled in the art for producing recombinant molecules or cells.

The teaching according to the invention can be carried out both with the use of isolated enzymes, and using whole cell catalysts. In a preferred embodiment, the expression "whole cell catalyst", as used herein, is taken to mean an intact, viable and metabolically active cell which provides the desired enzymatic activity. The whole cell catalyst can either transport the substrate that is to be metabolized, in the case of the present invention, the alcohol, or the oxidation product formed therefrom, into the cell interior, where it is metabolized by cytosolic enzymes, or it can present the enzyme of interest on its surface where it is directly exposed to substrates in the medium. Numerous systems for producing whole cell catalysts are known to those skilled in the art, for example from DE 60216245.

For a number of applications, the use of isolated enzymes is advisable. In a preferred embodiment, the expression "isolated", as used herein, means that the enzyme is present in a purer and/or more concentrated form than in its natural source. In a preferred embodiment, the enzyme is considered to be isolated if it is a polypeptide enzyme and makes up more than 60, 70, 80, 90 or preferably 95% of the mass protein fraction of the corresponding preparation. Those skilled in the art know numerous methods for measuring the mass of a protein in a solution, for example visual estimation on the basis of the thickness of corresponding protein bands on SDS polyacrylamide gels, NMR spectroscopy or mass-spectrometry-based methods.

The enzymatically catalyzed reactions of the method according to the invention are typically carried out in a solvent or solvent mixture having a high water fraction, preferably in the presence of a suitable buffer system for establishing a pH compatible with enzymatic activity. In the case of hydrophobic reactants, in particular in the case of alcohols having a carbon chain comprising more than three carbon atoms, however, the additional presence of an organic cosolvent is advantageous, which organic cosolvent can mediate the contact of the enzyme with the substrate. The one or more than one cosolvent is present in a total fraction of the solvent mixture of, or less than, 95, 90, 85, 80, 75, 70, 65, 60, 55, 50 45, 40, 35, 30, 25, 20, 15, 10 or 5 percent by volume.

The hydrophobicity of the cosolvent plays an important role here. It may be represented by log P, the logarithm to base 10 of the n-octanol-water distribution coefficient. A preferred cosolvent has a log P of greater than −1.38, more preferably from −1 to +2, still more preferably from 0 to 1.5.

The n-octanol-water distribution coefficient $K^{ow}$ or P is a dimensionless distribution coefficient which indicates the ratio of the concentrations of a substance in a two-phase system of 1-octanol and water (see J. Sangster, *Octanol-Water Partition Coefficients: Fundamentals and Physical Chemistry*, Vol. 2 of *Wiley Series in Solution Chemistry*, John Wiley & Sons, Chichester, 1997). Stated more precisely, the $K^{ow}$ or P designates the ratio of the concentration of the substance in the octanol-rich phase to the concentration thereof in the water-rich phase.

The $K^{ow}$ value is a model index for the ratio between lipophilicity (fat solubility) and hydrophilicity (water solubility) of a substance. There is the expectation, using the distribution coefficient of a substance in the octanol-water system, of also being able to estimate the distribution coefficients of this substance in other systems having an aqueous phase. $K^{ow}$ is greater than one if a substance is more soluble in fatty solvents such as n-octanol, and is less than one if it is more soluble in water. Correspondingly, Log P is positive for lipophilicity and negative for hydrophilic substances. Since $K^{ow}$ cannot be measured for all chemicals, there are very varied models for the prediction thereof, e.g. by quantitative structure-activity relationships (QSAR) or by linear free energy relationships (LFER), described, for example, in Eugene Kellogg G, Abraham D J: Hydrophobicity: is Log P(o/w) more than the sum of its parts?. Eur J Med Chem. 2000 July-August; 35(7-8):651-61 or Gudrun Wienke, "Messung and Vorausberechnung von n-Octanol/Wasser-Verteilungskoeffizienten" [Measurement and forecast of n-octanol/water distribution coefficients], doctoral thesis, Univ. Oldenburg, 1-172, 1993.

In the context of the present application, log P is determined by the method of Advanced Chemistry Development Inc., Toronto, using the programme module ACD/Log P DB.

A preferred cosolvent has a log P of greater than −1.38, more preferably from −1 to +2, still more preferably from −0.75 to 1.5, or −0.5 to 0.5, or −0.4 to 0.4, or −0.3 to −0.1. In a preferred embodiment, the cosolvent is a dialkyl ether of the formula $Alk_1$-O-$Alk_2$ having a log P of greater than −1.38, more preferably from −1 to +2, still more preferably from 0 to 1.5, wherein the two alkyl substituents $Alk_1$ and $Alk_2$ are each, and independently of one another, selected from the group which consists of methyl, ethyl, propyl, butyl, isopropyl and tert-butyl. In a particularly preferred embodiment, the cosolvent is methyl tertiary butyl ether (MTBE). In the most preferred embodiment, the cosolvent is dimethoxyethane (DME). In a further preferred embodiment, the cosolvent is a compound of the formula $R^3$—O—$(CH_2)_x$—O—$R^4$, wherein $R^3$ and $R^4$ are each, and independently of one another, selected from the group consisting of methyl, ethyl, propyl and butyl, and x is 1 to 4, wherein preferably $R^3$ and $R^4$ are each methyl and x is 2.

In a further preferred embodiment, the cosolvent is a carboxylic acid or fatty acid, preferably a fatty acid having at least 6, more preferably at least 12, carbon atoms. The fatty acid can be a saturated fatty acid, for example lauric acid, myristic acid, palmitic acid, margaric acid, stearic acid, arachic acid or behenic acid, or an unsaturated fatty acid, for example myristoleic acid, palmitoleic acid, petroselinic acid, oleic acid, elaidic acid, vaccenic acid, gadoleic acid, icosenoic acid or erucic acid. Mixtures of various fatty acids are equally possible, for example globe thistle oil which principally contains unsaturated fatty acids. Since not all fatty acids are soluble to a significant extent at room temperature, it may be necessary to resort to further measures, such as increasing the temperature, for example, or, more preferably, adding a further solvent in order to make it accessible to the aqueous phase. In a particularly preferred embodiment, a fatty acid or an ester thereof, preferably the methyl ester, most preferably lauric acid methyl ester, is used as such a further solvent.

The enzymatic cascade according to the invention can proceed according to the invention in the presence of an alanine dehydrogenase. It is a particular strength of the present invention that this configuration permits a reduction-equivalent neutral reaction procedure, i.e. the reaction proceeds without supply or removal of electrons in the form of reduction equivalents, since the NADH generated by the alcohol dehydrogenase in the course of alcohol oxidation is consumed in the generation of alanine, with consumption of an inorganic nitrogen donor, preferably ammonia, or an ammonia source.

In a preferred embodiment, the expression "alanine dehydrogenase", as used herein, is taken to mean an enzyme which catalyzes the conversion of L-alanine, with consumption of water and $NAD^+$ to form pyruvate, ammonia and NADH. Preferably, the alanine dehydrogenase is an intracellular alanine dehydrogenase, still more preferably, a recombinant intracellular alanine dehydrogenase of a bacterial whole cell catalyst.

In a preferred embodiment, a whole cell catalyst having all of the required activities is used for the method according to the invention, i.e. $NAD(P)^+$-dependent alcohol dehydrogenase, transaminase and optionally monooxygenase and/or alanine dehydrogenase. The use of such a whole cell catalyst has the advantage that all of the activities are used in the form of a single agent and it is not necessary to prepare enzymes in a biologically active form on a large scale. Suitable methods for the construction of whole cell catalysts are known to those skilled in the art, in particular the construction of plasmid systems for the expression of one or more as a recombinant protein or the integration of the DNA encoding the required recombinant protein into the chromosomal DNA of the host cell used.

The features of the invention disclosed in the preceding description, claims and drawings can be important in the various embodiments thereof not only individually, but also in any desired combination for implementing the invention.

BRIEF DESCRIPTION OF THE DRAWING

FIG. 1 shows an exemplary alignment comprising various transaminases (SEQ ID NOS: 1-19, respectively), in particular that of *Chromobacterium violaceum* ATCC 12472 (database code NP_901695, "TACV_co" (SEQ ID NO: 1)). The amino acid residues corresponding to the positions Val224 and (4230 of the latter transaminase are underlined in all the sequences. The alignment was prepared using Clustal W2. The sequences are as follows:

TACV_co=SEQ ID NO: 1
Q1GD43_3FCR_=SEQ ID NO: 2
Q987B2_3GJU_=SEQ ID NO: 3
Q31WE9_315T_=SEQ ID NO: 4
1.5.020=SEQ ID NO: 5
1.5.021=SEQ ID NO: 6
Ade=SEQ ID NO: 7
TA_R.eu=SEQ ID NO: 8
TA5_Pao132 SEQ ID NO: 9
P28269_3A8U_=SEQ ID NO: 10
P0A4X6_3BV0_=SEQ ID NO: 11
P12995_1S0A_=SEQ ID NO: 12
P53555_3DOD_=SEQ ID NO: 13
1.5.017=SEQ ID NO: 14
Aci=SEQ ID NO: 15
Bme=SEQ ID NO: 16
TA_Aci_mut=SEQ ID NO: 17
pCR05=SEQ ID NO: 18
P16932_IZOD_=SEQ ID NO: 19

EXAMPLE 1

Amination of Various Substrates Using an $NAD^+$-Dependent Alcohol Dehydrogenase in Comparison with the Alcohol Dehydrogenase AlkJ, Using the Method According to the Invention Substrates:
The substrates used were hexane-1,6-diol (1), 6-aminohexan-1-ol (2) and ethyl-6-hydroxyhexanoate (3).
Enzymes:
Alanine Dehydrogenase:
The L-alanine dehydrogenase of *Bacillus subtilis* was expressed in *E. coli*. First, an overnight culture was prepared which was then used to inoculate the main culture (LB-ampicillin medium). The cells were incubated on a shaker for 24 hours at 30° C. and 120 rpm. Then IPTG (0.5 mM, isopropyl β-D-1-thiogalactopyranoside, Sigma) was added under sterile conditions for induction, and the cultures were shaken for a further 24 hours at 20° C.

The cells were centrifuged off (8000 rpm, 20 min 4° C.), washed, and the supernatant was discarded. The cells were then disrupted using ultrasound (1 s pulse, 4 s pause, time: 10 min, amplitude: 40%), the mixture was centrifuged (20 min, 18000 rpm, 4° C.) and the enzyme was purified, using a His-prep column.
Alcohol Dehydrogenase of *Bacillus stearothermophilus* (ADH-hT; P42328.1))

For preparation of the $NAD^+$-dependent alcohol dehydrogenase of *Bacillus stearothermophilus* (Fiorentino G, Cannio R, Rossi M, Bartolucci S: Decreasing the stability and changing the substrate specificity of the *Bacillus stearothermophilus* alcohol dehydrogenase by single amino acid replacements. Protein Eng 1998, 11: 925-930), first an overnight culture was prepared (10 ml of LB/ampicillin medium, ampicillin 100 μg/ml, 30° C., 120 rpm) which was then used to inoculate culture vessels which in turn were shaken for about 12 hours at 37° C. and 120 rpm. The cells were centrifuged off (8000 rpm, 20 minutes, 4° C.), washed, the supernatant was discarded and the pellet lyophilized. Finally, the cells were disrupted, using ultrasound (1 s pulse, 4 s pause, time: 10 min, amplitude: 40%), and the mixture was centrifuged (20 min, 18000 rpm, 4° C.) and used as a crude extract. The protein concentration was estimated by SDS-PAGE.

AlkJ-Alcohol Dehydrogenase (from *Pseudomonas oleovirans* Gpo1):

The enzyme was prepared under the same conditions as the alcohol dehydrogenase of *Bacillus stearothermophilus*, except that the plasmid pTZE03_AlkJ (SEQ ID NO 20) was used and canamycin was used as antibiotic (50 µg/ml). The protein concentration was likewise estimated by SDS-PAGE.

Transaminase CV-ωTA from *Chromobacterium violaceum*:

For preparation of CV-ωTA from *Chromobacterium violaceum* (U. Kaulmann, K. Smithies, M. E. B. Smith, H. C. Hailes, J. M. Ward, *Enzyme Microb. Technol.* 2007, 41, 628-637; b) M. S. Humble, K. E. Cassimjee, M. Håkansson, Y. R. Kimbung, B. Walse, V. Abedi, H.-J. Federsel, P. Berglund, D. T. Logan, *FEBS Journal* 2012, 279, 779-792; c) D. Koszelewski, M. Göritzer, D. Clay, B. Seisser, W. Kroutil, *ChemCatChem* 2010, 2, 73-77), an overnight culture was first prepared (LB/ampicillin medium, 30° C., 120 rpm) which was then used to inoculate culture flasks with the same medium which were shaken for about three hours at 37° C. and 120 rpm until an optical density at 600 nm of 0.7 was achieved. Then, IPTG stock solution (0.5 mM) was added for the induction at 20° C. and 120 rpm for three hours. The cells were centrifuged off, the supernatant was discarded and the cells were stored at 4° C. Finally, the cells were disrupted using ultrasound (1 s pulse, 4 s pause, time: 10 min, amplitude: 40%), the mixture was centrifuged (20 min, 18000 rpm, 4° C.) and the supernatant was used as a crude extract.

Experimental Procedure:

The experimental solution is described in Tab. 1.

TABLE 1

| | Experimental solution | |
|---|---|---|
| Experimental solution | ADH-hT (crude) | 200 µl |
| | Transaminase | 200 µl |
| | AlaDH | 10 µl |
| | | (250 U) |
| | L-Alanine | 22.3 mg |
| | | (250 µmol) |
| | NAD$^+$ | 0.5 mg |
| | | (0.75 µmol) |
| | NH$_4$Cl | 21 mg |
| | | (500 µmol) |
| | PLP | 0.1 mg |
| | | (0.35 µmol) |
| | NaOH 6M | 7.5 µl |
| | H$_2$O/cosolvent | 400 µl |
| | Substrate | 50 µmol |
| | pH at the end | 8.5 |
| | Total volume | 1.22 mL |

The substrate is dissolved in the appropriate amount of cosolvent (see Tab. 2) and L-alanine dissolved in 300 µl of water was added. In 75 µl of water, ammonium chloride was added. NAD$^+$ and PLP dissolved in 25 µl of water in each case were added. The pH was adjusted by adding 7.5 µl of a 6 M NaOH solution. The transaminase and alanine dehydrogenase were added. The reaction was started by adding alcohol dehydrogenase. After 22 hours the reaction was stopped by adding the derivatization reagents stated below.

Derivatization of Amines:

200 µl of triethylamine and ESOF (ethyl succinimidooxy formate) (80 or 40 mg) in acetonitrile (500 µl) were added to a sample of 500 µl. The samples were then shaken for one hour at 45° C. and then extracted with dichloromethane, dried over sodium sulfate and measured using GC-MS. If no alanine dehydrogenase was employed, then to an aqueous solution L-alanine (500 mM), NAD$^+$ (2 mM) and PLP (0.5 mM) at a pH of 8.5 (adjusted by adding NaOH) and substrate in DME (120 µl, 25 mM) were added. The reaction was started by adding 200 µl each of alcohol dehydrogenase (NAD$^+$-dependent) or AlkJ) and transaminase. The samples were shaken at 25° C. and 300 rpm for 24 hours. The samples were processed as described above and analyzed by GC-MS.

Results:

TABLE 2

Amination in the absence of alanine dehydrogenase. The substrates are hexane-1,6-diol (1), 6-aminohexan-1-ol (2) and ethyl 6-hydroxyhexanoate (3).

| Substrate | Oxidizing enzyme | Transaminase | Unreacted substrate [%] | Product [%] |
|---|---|---|---|---|
| 1 | AlkJ | CV | >99 | <1 (monoamine) |
| | | | | <1 (diamine) |
| 1 | ADH-hT | CV | <1 | <99 (monoamine) |
| | | | | >1 (diamine) |
| 1 | — | — | >99 | <1 |
| 2 | AlkJ | CV | 91 | 9 |
| 2 | ADH-hT | CV | 76 | 24 |
| 2 | — | — | >99 | <1 |
| 3 | AlkJ | CV | 99 | 1 |
| 3 | ADH-hT | CV | 22 | 78 |
| 3 | — | — | >99 | <1 | n.d. not detected

TABLE 3

Amination in the presence of alanine dehydrogenase. The substrates are hexane-1,6-diol (1), 6-aminohexan-1-ol (2) and ethyl 6-hydroxyhexanoate (3).

| Substrate | Oxidizing enzyme | Transaminase | Unreacted substrate [%] | Product [%] |
|---|---|---|---|---|
| 1 | AlkJ | CV | >99 | <1 (monoamine) |
| | | | | <1 (diamine) |
| 1 | ADH-hT | CV | <1 | 92 (monoamine) |
| | | | | 8 (diamine) |
| 1 | — | — | >99 | <1 (monoamine) |
| | | | | <1 (diamine) |
| 2 | AlkJ | CV | >99 | <1 |
| 2 | ADH-hT | CV | 19 | 81 |
| 2 | — | — | >99 | <1 |
| 3 | AlkJ | CV | >99 | <1 |
| 3 | ADH-hT | CV | <1 | >99 |
| 3 | — | — | >99 | <1 |

For a number of structurally differing substrates, namely hexane-1,6-diol (1), 6-aminohexan-1-ol (2) and ethyl 6-hydroxyhexanoate (3), it was found in each case that the reaction proceeds markedly more efficiently using the NAD$^+$-dependent alcohol dehydrogenase of *Bacillus stearothermophilus* than with the use of alcohol dehydrogenase AlkJ. It was possible to show this surprising technical effect equally in the presence and absence of alanine dehydrogenase.

Summary:

EXAMPLE 2

Amination of Various Alcohol Substrates

In order to confirm that the enzyme system according to the invention converts a variety of structurally different substrates, further alkanols and alkanediols were converted in vitro using suitable enzymes to the corresponding amines or diamines. It was found that the alcohol dehydrogenase from horse liver (HL-ADH, E-isoenzyme; NP_001075997.1) and the alcohol dehydrogenase from *Bacillus stearothermophilus* (ADH-hT; P42328.1) are equally suitable. Two different aminases, namely those from *Chromobacterium violaceum*[16] (CV-ωTA) and a variant of an (S)-selective ω-TA from *Arthrobacter citreus* (ArS-ωTA) (A. R. Martin, R. DiSanto, I. Plotnikov, S. Kamat, D. Shonnard, S. Pannuri, *Biochem. Eng. J.* 2007, 37, 246-255) were used. The alanine dehydrogenase was from *Bacillus subtilis* (F. G. Mutti, C. S. Fuchs, D. Pressnitz, J. H. Sattler, W. Kroutil, *Adv. Synth. Catal.* 2011, 353, 3227-3233).

The products were derivatized with ethyl (succinimidooxy)formate (I. Edafiogho, K. R. Scott, J. A. Moore, V. A. Famar, J. M. Nicholson, *J. Med. Chem.* 1991, 34, 387-392) and detected by GC-MS using an Agilent J&W HP-5 column (30 m, 320 μm, 0.25 μm).

TABLE 4

Amination of primary alcohols

| No. | Substrate | c [%] | Aldehyde [%] | Amines [%] |
|---|---|---|---|---|
| 1 | 1-Hexanol | >99 | <1 | >99 |
| 2 | 1-Octanol | 50 | <1 | 50 |
| 3 | 1-Octanol | 57[b] | <1 | 57 |
| 4 | 1-Decanol | 2 | <1 | 2 |
| 5 | 1-Decanol | 25[b] | <1 | 25 |
| 6 | 1-Dodecanol | 10[b] | <1 | 10 |

[a]Reaction conditions: substrate (50 mM), CV-ωTA (1 mg, 0.2 U) and ADH-hT (1 mg, 0.25 U), AlaDH (0.4 mg, 0.25 U), PLP (0.35 mM), NAD$^+$ (0.75 mM), and ammonium chloride (275 mM), L-alanine (250 mM), pH 8.5, 24 hours, 20° C.
[b]1,2-dimethoxyethane (10% v v$^{-1}$) was added as co-solvent.

TABLE 5

Amination of 1,ω-diols[c]

| No. | Sub. | Solvent | Vol. Solv. [%] | T. [°C.] | c [%] | Monoamine [%] | Diamine [%] |
|---|---|---|---|---|---|---|---|
| 1 | 1,8-octanediol | MTBE | 30 | 35[d] | 52 | 49 | 3 |
| 2 | 1,8-octanediol | MTBE | 30 | 25 | 98 | 52 | 46 |
| 3 | 1,8-octanediol | DME | 40 | 25 | 95 | 80 | 15 |
| 4 | 1,8-octanediol | DME | 30 | 25 | >99 | 18 | 82 |
| 5 | 1,8-octanediol | DME | 20 | 25 | 99 | 16 | 83 |
| 6 | 1,8-octanediol | DME | 10 | 25 | 99 | 1 | 98 |
| 7 | 1,8-octanediol | DME | 10 | 20 | >99 | <1 | >99 |
| 8 | 1,10-decanediol | DME | 20 | 25 | 99 | 6 | 93 |
| 9 | 1,10-decanediol | DME | 20 | 20 | >99 | 2 | 98 |
| 10 | 1,10-decanediol | DME | 10 | 20 | >99 | 1 | 99 |

[c]General reaction conditions: substrate (50 mM), CV-ωTA (1 mg, 0.25 U) and ADH-hT (1 mg, 0.2 U), AlaDH (0.1 mg, 0.7 U), PLP (0.35 mM), NAD$^+$ (0.75 mM), ammonium chloride (275 mM), L-alanine (250 mM), pH 8.5.
[d]ArS-ωTA used instead of CV-ωTA.

LITERATURE REFERENCES

PCT/EP/2008/067447 (2009): ω-AMINO CARBOXYLIC ACIDS, ω-AMINO CARBOXYLIC ACID ESTERS, OR RECOMBINANT CELLS WHICH PRODUCE LACTAMS THEREOF

C. Grant, J. M. Woodley and F. Baganz (2011), *Enzyme and Microbial Technology* 48, 480-486

Gudrun Wienke, "Messung and Vorausberechnung von n-Octanol/Wasser-Verteilungskoeffizienten" [Measurement and prediction of n-octanol/water distribution coefficients], doctoral thesis, Univ. Oldenburg, 1-172, 1993

DE 60216245 (2007): FUNKTIONELLES OBERFLÄCHENDISPLAY VON POLYPEPTIDEN [FUNCTIONAL SURFACE DISPLAY OF POLYPEPTIDES]

Sambrook/Fritsch/Maniatis (1989): Molecular Cloning: A Laboratory Manual, Cold Spring Harbor Laboratory Press, 2$^{nd}$ edition J. Sangster, *Octanol-Water Partition Coefficients: Fundamentals and Physical Chemistry*, Vol. 2 of *Wiley Series in Solution Chemistry*, John Wiley & Sons, Chichester, 1997

Eugene Kellogg G, Abraham D J: Hydrophobicity: is Log P(o/w) more than the sum of its parts?. Eur J Med Chem. 2000 July-August; 35(7-8):651-61

Larkin M A, Blackshields G, Brown N P, Chema R, McGettigan P A, McWilliam H, Valentin F, Wallace I M, Wilm A, Lopez R, Thompson J D, Gibson T J and Higgins D G Bioinformatics 2007 23(21):2947-2948.

Goujon M, McWilliam H, Li W, Valentin F, Squizzato S, Paern J, Lopez R (2010) *Nucleic acids research July*, 38 Suppl: W695-9

The invention claimed is:

1. A method for producing an amine or a diamine, comprising:
   (a) contacting a primary alcohol of the formula HO—(CH)—R$^1$,
   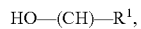

with an NAD(P)$^+$-dependent alcohol dehydrogenase to oxidize said primary alcohol to form an aldehyde or ketone oxidation product, wherein R$^1$ is selected from the group consisting of —OH, —SH, —NH$_2$ and —COOR$^2$, x is at least 3 and R$^2$ is selected from the group consisting of H, alkyl and aryl; and
   (b) contacting said aldehyde or ketone oxidation product with a transaminase to transfer α-amino groups from an amino acid to an α-ketocarboxylic acid to produce said amine or said diamine,
   wherein said NAD(P)$^+$-dependent alcohol dehydrogenase, said transaminase, or both, are a recombinant or isolated enzyme.

2. The method of claim 1, further comprising hydroxylating an alkane of the formula H—(CH$_2$)$_x$—R$^1$

by contacting said alkane with a monooxygenase to produce said primary alcohol of the formula HO—(CH)—R$^1$, wherein R$^1$ has the same meaning as defined above.

3. The method of claim 1, wherein said NAD(P)$^+$-dependent alcohol dehydrogenase is an NAD(P)$^+$-dependent alcohol dehydrogenase having zinc as a cofactor.

4. The method of claim 3, wherein said NAD(P)$^+$-dependent alcohol dehydrogenase is a *Bacillus stearothermophilus* NAD(P)$^+$-dependent alcohol dehydrogenase.

5. The method of claim 2, wherein monooxygenase is selected from the group consisting of *Pseudomonas putida* AlkBGT, *Candida tropicales* cytochrome P450, and *Cicer arietinum* cytochrome P450.

6. The method of claim 1, wherein said transaminase is selected from the group consisting of:
   (a) a *Chromobacterium violaceum* ATCC 12472 transaminase, wherein in said transaminase an amino acid corresponding to the amino acid residue at position 23 of the amino acid sequence of SEQ ID NO: 1 is isoleucine, valine, phenylalanine, methionine, or leucine; and
   (b) a *Chromobacterium violaceum* ATCC 12472 transaminase, wherein in said transaminase an amino acid corresponding to the amino acid residue at position 29 of the amino acid sequence of SEQ ID NO: 1 is an amino acid other than threonine.

7. The method of claim 1, wherein steps (a), (b), or both, are carried out in the presence of an isolated or recombinant alanine dehydrogenase and an inorganic nitrogen source, wherein said alanine dehydrogenase catalyzes the conversion of L-alanine, with consumption of water and NAD$^+$, to form pyruvate, ammonia and NADH.

8. The method of claim 1, wherein at least one of said NAD(P)$^+$-dependent alcohol dehydrogenase and said transaminase are a recombinant enzyme and are in the form of a whole cell catalyst comprising said enzyme.

9. The method of claim 8, wherein both of said NAD(P)$^+$-dependent alcohol dehydrogenase and said transaminase are in the form of a whole cell catalyst.

10. The method of claim 1, wherein said step (a) further comprises the presence of an organic cosolvent having a log P of greater than −1.38.

11. The method of claim 10, wherein said organic cosolvent is selected from unsaturated fatty acids.

12. The method of claim 10, wherein said organic cosolvent is a compound of the formula $$R^1-O-(CH_2)_x-O-R^4,$$

wherein $R^3$ and $R^4$ are each independently of one another, selected from the consisting of methyl, ethyl, propyl and butyl, and x is 1 to 4.

13. A method for producing an amine or a diamine, comprising
(a) providing a whole cell catalyst comprising a recombinant NAD(P)$^+$-dependent alcohol dehydrogenase, a recombinant transaminase, optionally a recombinant monooxygenase, and optionally a recombinant alanine dehydrogenase
(b) contacting a primary alcohol of the formula $$HO-(CH_2)_x-R^1$$

with said whole cell catalyst, wherein said recombinant NAD(P)$^+$-dependent alcohol dehydrogenase present in said whole cell catalyst oxidizes said primary alcohol to form an aldehyde or ketone oxidation product, said recombinant transaminase present in said whole cell catalyst transfers α-amino groups from an amino acid to an α-ketocarboxylic acid to produce said amine or said diamine, said optional alanine dehydrogenase catalyzes the conversion of L-alanine, with consumption of water and NAD$^+$, to form pyruvate, ammonia and NADH, said optional monooxygenase hydroxylates an alkane of the formula $H-(CH_2)_x-R^1$ to produce said primary alcohol wherein $R^1$ is selected from the group consisting of —OH, —SH, —NH$_2$, and —COOR$^2$, x is at least 3 and $R^2$ is selected from the group consisting of H, alkyl and aryl.

14. The method of claim 13, wherein step (b) is performed in the presence of an organic cosolvent having a log P of greater than −1.38.

15. The method of claim 14, wherein said organic cosolvent is selected from unsaturated fatty acids.

16. The method of claim 10, wherein said organic cosolvent has a log P of 0 to 1.2.

17. The method of claim 11, wherein said organic cosolvent is oleic acid.

18. The method of claim 2, wherein said monooxygenase is a recombinant or isolated enzyme.

19. The method of claim 8, wherein the whole cell catalyst further comprises a recombinant or isolated monooxygenase and alanine dehydrogenase, wherein said monooxygenase hydroxylates an alkane of the formula $H-(CH_2)_x-R^1$ to produce said primary alcohol and said alanine dehydrogenase catalyzes the conversion of L-alanine, with consumption of water and NAD$^+$, to form pyruvate, ammonia and NADH.

* * * * *

SEQUENCE LISTING

<160> NUMBER OF SEQ ID NOS: 20

<210> SEQ ID NO 1
<211> LENGTH: 57
<212> TYPE: PRT
<213> ORGANISM: Artificial Sequence
<220> FEATURE:
<223> OTHER INFORMATION: Aligned sequence of transaminase TACV_co in Figure 1

```
<400> SEQUENCE: 1

Val Val Ala Ala Arg Trp Leu Glu Glu Lys Ile Leu Glu Ile Gly Ala
1               5                   10                  15

Asp Lys Val Ala Ala Phe Val Gly Glu Pro Ile Gln Gly Ala Gly Gly
                20                  25                  30

Val Ile Val Pro Pro Ala Thr Tyr Trp Pro Glu Ile Glu Arg Ile Cys
            35                  40                  45

Arg Lys Tyr Asp Val Leu Leu Val Ala
            50                  55

<210> SEQ ID NO 2
<211> LENGTH: 57
<212> TYPE: PRT
<213> ORGANISM: Artificial Sequence
<220> FEATURE:
<223> OTHER INFORMATION: Aligned sequence of transaminase Q1GD43_3FCR_
      in Figure 1

<400> SEQUENCE: 2

Ala His Cys Val Ala Glu Leu Glu Ala Leu Ile Glu Arg Glu Gly Ala
1               5                   10                  15

Asp Thr Ile Ala Ala Phe Ile Gly Glu Pro Ile Leu Gly Thr Gly Gly
                20                  25                  30

Ile Val Pro Pro Ala Gly Tyr Trp Glu Ala Ile Gln Thr Val Leu
            35                  40                  45

Asn Lys His Asp Ile Leu Leu Val Ala
            50                  55

<210> SEQ ID NO 3
<211> LENGTH: 57
<212> TYPE: PRT
<213> ORGANISM: Artificial Sequence
<220> FEATURE:
<223> OTHER INFORMATION: Aligned sequence of transaminase Q987B2_3GJU_
      in Figure 1

<400> SEQUENCE: 3

Gln His Cys Ala Asp Lys Leu Glu Glu Met Ile Leu Ala Glu Gly Pro
1               5                   10                  15

Glu Thr Ile Ala Ala Phe Ile Gly Pro Ile Leu Gly Thr Gly Gly
                20                  25                  30

Ile Val Pro Pro Ala Gly Tyr Trp Glu Lys Ile Gln Ala Val Leu
            35                  40                  45

Lys Lys Tyr Asp Val Leu Leu Val Ala
            50                  55

<210> SEQ ID NO 4
<211> LENGTH: 57
<212> TYPE: PRT
<213> ORGANISM: Artificial Sequence
<220> FEATURE:
<223> OTHER INFORMATION: Aligned sequence of transaminase Q3IWE9_3I5T_
      in Figure 1

<400> SEQUENCE: 4

Asp Asp Leu Val Gln Glu Phe Glu Asp Arg Ile Glu Ser Leu Gly Pro
1               5                   10                  15

Asp Thr Ile Ala Ala Phe Leu Ala Glu Pro Ile Leu Ala Ser Gly Gly
                20                  25                  30
```

Val Ile Ile Pro Pro Ala Gly Tyr His Ala Arg Phe Lys Ala Ile Cys
            35                  40                  45

Glu Lys His Asp Ile Leu Tyr Ile Ser
    50                  55

<210> SEQ ID NO 5
<211> LENGTH: 57
<212> TYPE: PRT
<213> ORGANISM: Artificial Sequence
<220> FEATURE:
<223> OTHER INFORMATION: Aligned sequence of transaminase 1.5.020 in
      Figure 1

<400> SEQUENCE: 5

Ala Glu Leu Ala Asn Glu Leu Glu Arg Ile Val Ala Leu His Asp Ala
1               5                   10                  15

Ser Thr Ile Ala Ala Val Ile Val Glu Pro Val Ala Gly Ser Thr Gly
            20                  25                  30

Val Ile Leu Pro Pro Lys Gly Tyr Leu Gln Lys Leu Arg Glu Ile Cys
            35                  40                  45

Thr Lys His Gly Ile Leu Leu Ile Phe
    50                  55

<210> SEQ ID NO 6
<211> LENGTH: 57
<212> TYPE: PRT
<213> ORGANISM: Artificial Sequence
<220> FEATURE:
<223> OTHER INFORMATION: Aligned sequence of transaminase 1.5.021 in
      Figure 1

<400> SEQUENCE: 6

Ala Glu Leu Ala Asn Glu Leu Glu Arg Ile Val Ala Leu His Asp Ala
1               5                   10                  15

Ser Thr Ile Ala Ala Val Ile Val Glu Pro Val Ala Gly Ser Thr Gly
            20                  25                  30

Val Ile Leu Pro Pro Lys Gly Tyr Leu Gln Lys Leu Arg Glu Ile Cys
            35                  40                  45

Thr Lys His Gly Ile Leu Leu Ile Phe
    50                  55

<210> SEQ ID NO 7
<211> LENGTH: 57
<212> TYPE: PRT
<213> ORGANISM: Artificial Sequence
<220> FEATURE:
<223> OTHER INFORMATION: Aligned sequence of transaminase Ade in
      Figure 1

<400> SEQUENCE: 7

Ala His Leu Ala Asp Glu Leu Glu Arg Ile Ile Ala Leu His Asp Ala
1               5                   10                  15

Ser Thr Ile Ala Ala Val Ile Val Glu Pro Met Ala Gly Ser Thr Gly
            20                  25                  30

Val Leu Val Pro Pro Lys Gly Tyr Leu Glu Lys Leu Arg Glu Ile Thr
            35                  40                  45

Ala Arg His Gly Ile Leu Leu Ile Phe
    50                  55

```
<210> SEQ ID NO 8
<211> LENGTH: 57
<212> TYPE: PRT
<213> ORGANISM: Artificial Sequence
<220> FEATURE:
<223> OTHER INFORMATION: Aligned sequence of transaminase TA_R.eu in
      Figure 1

<400> SEQUENCE: 8

Ala His Leu Ala Asp Glu Leu Glu Arg Ile Val Ala Leu His Asp Pro
1               5                   10                  15

Ser Thr Ile Ala Ala Val Ile Val Glu Pro Leu Ala Gly Ser Ala Gly
            20                  25                  30

Val Leu Val Pro Pro Val Gly Tyr Leu Asp Lys Leu Arg Glu Ile Thr
        35                  40                  45

Thr Lys His Gly Ile Leu Leu Ile Phe
    50                  55

<210> SEQ ID NO 9
<211> LENGTH: 57
<212> TYPE: PRT
<213> ORGANISM: Artificial Sequence
<220> FEATURE:
<223> OTHER INFORMATION: Aligned sequence of transaminase TA5_Pao132 in
      Figure 1

<400> SEQUENCE: 9

Val Glu Leu Ala Asn Glu Leu Leu Lys Leu Ile Glu Leu His Asp Ala
1               5                   10                  15

Ser Asn Ile Ala Ala Val Ile Val Glu Pro Met Ser Gly Ser Ala Gly
            20                  25                  30

Val Leu Val Pro Pro Val Gly Tyr Leu Gln Arg Leu Arg Glu Ile Cys
        35                  40                  45

Asp Gln His Asn Ile Leu Leu Ile Phe
    50                  55

<210> SEQ ID NO 10
<211> LENGTH: 57
<212> TYPE: PRT
<213> ORGANISM: Artificial Sequence
<220> FEATURE:
<223> OTHER INFORMATION: Aligned sequence of transaminase P28269_3A8U_
      in Figure 1

<400> SEQUENCE: 10

Ile Ala Leu Ala Asp Glu Leu Leu Lys Leu Ile Glu Leu His Asp Ala
1               5                   10                  15

Ser Asn Ile Ala Ala Val Phe Val Glu Pro Leu Ala Gly Ser Ala Gly
            20                  25                  30

Val Leu Val Pro Pro Glu Gly Tyr Leu Lys Arg Asn Arg Glu Ile Cys
        35                  40                  45

Asn Gln His Asn Ile Leu Leu Val Phe
    50                  55

<210> SEQ ID NO 11
<211> LENGTH: 57
<212> TYPE: PRT
<213> ORGANISM: Artificial Sequence
<220> FEATURE:
<223> OTHER INFORMATION: Aligned sequence of transaminase P0A4X6_3BV0_
      in Figure 1
```

```
<400> SEQUENCE: 11

Pro Ala Tyr Ser Ala Ala Phe Glu Ala Gln Leu Ala Gln His Ala Gly
1               5                   10                  15

Glu Leu Ala Ala Val Val Glu Pro Val Val Gln Gly Ala Gly Gly
            20                  25                  30

Met Arg Phe His Asp Pro Arg Tyr Leu His Asp Leu Arg Asp Ile Cys
            35                  40                  45

Arg Arg Tyr Glu Val Leu Leu Ile Phe
        50                  55

<210> SEQ ID NO 12
<211> LENGTH: 57
<212> TYPE: PRT
<213> ORGANISM: Artificial Sequence
<220> FEATURE:
<223> OTHER INFORMATION: Aligned sequence of transaminase P12995_1S0A_
      in Figure 1

<400> SEQUENCE: 12

Glu Arg Asp Met Val Gly Phe Ala Arg Leu Met Ala Ala His Arg His
1               5                   10                  15

Glu Ile Ala Ala Val Ile Ile Glu Pro Ile Val Gln Gly Ala Gly Gly
            20                  25                  30

Met Arg Met Tyr His Pro Glu Trp Leu Lys Arg Ile Arg Lys Ile Cys
            35                  40                  45

Asp Arg Glu Gly Ile Leu Leu Ile Ala
        50                  55

<210> SEQ ID NO 13
<211> LENGTH: 57
<212> TYPE: PRT
<213> ORGANISM: Artificial Sequence
<220> FEATURE:
<223> OTHER INFORMATION: Aligned sequence of transaminase P53555_3DOD_
      in Figure 1

<400> SEQUENCE: 13

Asp Gln Cys Leu Arg Glu Leu Ala Gln Leu Leu Glu Glu His His Glu
1               5                   10                  15

Glu Ile Ala Ala Leu Ser Ile Glu Ser Met Val Gln Gly Ala Ser Gly
            20                  25                  30

Met Ile Val Met Pro Glu Gly Tyr Leu Ala Gly Val Arg Glu Leu Cys
            35                  40                  45

Thr Thr Tyr Asp Val Leu Met Ile Val
        50                  55

<210> SEQ ID NO 14
<211> LENGTH: 54
<212> TYPE: PRT
<213> ORGANISM: Artificial Sequence
<220> FEATURE:
<223> OTHER INFORMATION: Aligned sequence of transaminase 1.5.017 in
      Figure 1

<400> SEQUENCE: 14

Ala Asn Glu Ile Asp Arg Ile Met Thr Trp Glu Leu Ser Glu Thr Ile
1               5                   10                  15

Ala Gly Val Ile Met Glu Pro Ile Ile Thr Gly Gly Gly Ile Leu Met
            20                  25                  30
```

Pro Pro Asp Gly Tyr Met Lys Lys Val Glu Asp Ile Cys Arg Arg His
        35                  40                  45

Gly Ala Leu Leu Ile Cys
    50

<210> SEQ ID NO 15
<211> LENGTH: 56
<212> TYPE: PRT
<213> ORGANISM: Artificial Sequence
<220> FEATURE:
<223> OTHER INFORMATION: Aligned sequence of transaminase Aci in
      Figure 1

<400> SEQUENCE: 15

Leu Leu Ser Val Lys Tyr Thr Arg Arg Met Ile Glu Asn Tyr Gly Pro
1               5                   10                  15

Glu Gln Val Ala Ala Val Ile Thr Glu Val Ser Gln Gly Ala Gly Ser
            20                  25                  30

Ala Met Pro Pro Tyr Glu Tyr Ile Pro Gln Phe Arg Lys Met Thr Lys
        35                  40                  45

Glu Leu Gly Val Leu Trp Ile Asn
    50                  55

<210> SEQ ID NO 16
<211> LENGTH: 56
<212> TYPE: PRT
<213> ORGANISM: Artificial Sequence
<220> FEATURE:
<223> OTHER INFORMATION: Aligned sequence of transaminase Bme in
      Figure 1

<400> SEQUENCE: 16

Leu Leu Ser Val Lys Tyr Thr Arg Arg Met Ile Glu Asn Tyr Gly Pro
1               5                   10                  15

Glu Gln Val Ala Ala Val Ile Thr Glu Val Ser Gln Gly Ala Gly Ser
            20                  25                  30

Ala Met Pro Pro Tyr Glu Tyr Ile Pro Gln Ile Arg Lys Met Thr Lys
        35                  40                  45

Glu Leu Gly Val Leu Trp Ile Asn
    50                  55

<210> SEQ ID NO 17
<211> LENGTH: 56
<212> TYPE: PRT
<213> ORGANISM: Artificial Sequence
<220> FEATURE:
<223> OTHER INFORMATION: Aligned sequence of transaminase TA_Aci_mut in
      Figure 1

<400> SEQUENCE: 17

Leu Leu Ser Val Lys Tyr Thr Arg Arg Met Ile Glu Asn Tyr Gly Pro
1               5                   10                  15

Glu Gln Val Ala Ala Val Ile Thr Glu Val Ser Gln Gly Val Gly Ser
            20                  25                  30

Thr Met Pro Pro Tyr Glu Tyr Val Pro Gln Ile Arg Lys Met Thr Lys
        35                  40                  45

Glu Leu Gly Val Leu Trp Ile Ser
    50                  55

```
<210> SEQ ID NO 18
<211> LENGTH: 56
<212> TYPE: PRT
<213> ORGANISM: Artificial Sequence
<220> FEATURE:
<223> OTHER INFORMATION: Aligned sequence of transaminase pCR05 in
      Figure 1

<400> SEQUENCE: 18

Lys Tyr Ala Ser Asp Val His Asp Leu Ile Gln Phe Gly Thr Ser Gly
1               5                   10                  15

Gln Val Ala Gly Phe Ile Gly Glu Ser Ile Gln Gly Val Gly Gly Ile
            20                  25                  30

Val Glu Leu Ala Pro Gly Tyr Leu Pro Ala Ala Tyr Asp Ile Val Arg
        35                  40                  45

Lys Ala Gly Gly Val Cys Ile Ala
    50                  55

<210> SEQ ID NO 19
<211> LENGTH: 57
<212> TYPE: PRT
<213> ORGANISM: Artificial Sequence
<220> FEATURE:
<223> OTHER INFORMATION: Aligned sequence of transaminase P16932_1ZOD_
      in Figure 1

<400> SEQUENCE: 19

Leu Ala Glu Leu Asp Tyr Ala Phe Asp Leu Ile Asp Arg Gln Ser Ser
1               5                   10                  15

Gly Asn Leu Ala Ala Phe Ile Ala Glu Pro Ile Leu Ser Ser Gly Gly
            20                  25                  30

Ile Ile Glu Leu Pro Asp Gly Tyr Met Ala Ala Leu Lys Arg Lys Cys
        35                  40                  45

Glu Ala Arg Gly Met Leu Leu Ile Leu
    50                  55

<210> SEQ ID NO 20
<211> LENGTH: 6949
<212> TYPE: DNA
<213> ORGANISM: Artificial Sequence
<220> FEATURE:
<223> OTHER INFORMATION: Plasmid ptZE03_aLKj

<400> SEQUENCE: 20
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttc tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaagccg tttctgtaat gaaggagaaa      660
actcaccgag gcagttccat aggatggcaa gatcctggta tcggtctgcg attccgactc     720
```

-continued

```
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg caacgctac    1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatcctttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt ttcctgtttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
```

```
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagcc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacg atgtacgact atataatcgt tggtgctgga    5100
tctgcaggat gtgtgcttgc taatcgtctt tcggccgacc cctctaaaag agtttgttta    5160
cttgaagctg ggccgcgaga tacgaatccg ctaattcata tgccgttagg tattgctttg    5220
ctttcaaata gtaaaagtt gaattgggct tttcaaactg cgccacagca aaatctcaac    5280
ggccggagcc ttttctggcc acgaggaaaa acgttaggtg gttcaagctc aatcaacgca    5340
atggtctata tccgagggca tgaagacgat taccacgcat gggagcaggc ggccggccgc    5400 tactgggtt ggtaccgggc tcttgagttg ttcaaaaggc ttgaatgcaa ccagcgattc    5460
gataagtccg agcaccatgg ggttgacgga gaattagctg ttagtgattt aaaatatatc    5520
```

```
aatccgctta gcaaagcatt cgtgcaagcc ggcatggagg ccaatattaa tttcaacgga    5580
gatttcaacg gcgagtacca ggacggcgta gggttctatc aagtaaccca aaaaaatgga    5640
caacgctgga gctcggcgcg tgcattcttg cacggtgtac tttccagacc aaatctagac    5700
atcattactg atgcgcatgc atcaaaaatt cttttgaag accgtaaggc ggttggtgtt     5760
tcttatataa agaaaaatat gcaccatcaa gtcaagacaa cgagtggtgg tgaagtactt    5820
cttagtcttg gcgcagtcgg cacgcctcac cttctaatgc tttctggtgt tggggctgca    5880
gccgagctta aggaacatgg tgtttctcta gtccatgatc ttcctgaggt ggggaaaaat    5940
cttcaagatc atttggacat cacattgatg tgcgcagcaa attcgagaga gccgataggt    6000
gttgctcttt cttcatccc tcgtggtgtc tcgggtttgt tttcatatgt gtttaagcgc     6060
gaggggtttc tcactagtaa cgtggcagag tcgggtggtt ttgtaaaaag ttctcctgat    6120
cgtgatcggc ccaatttgca gtttcatttc cttccaactt atcttaaaga tcacggtcga    6180
aaaatagcgg gtggttatgg ttatacgcta catatatgtg atcttttgcc taagagccga    6240
ggcagaattg gcctaaaaag cgccaatcca ttacagccgc ctttaattga cccgaactat    6300
cttagcgatc atgaagatat taaaaccatg attgcgggta ttaagatagg gcgcgctatt    6360
ttgcaggccc catcgatggc gaagcatttt aagcatgaag tagtaccggg ccaggctgtt    6420
aaaactgatg atgaaataat cgaagatatt cgtaggcgag ctgagactat ataccatccg    6480
gtaggtactt gtaggatggg taaagatcca gcgtcagttg ttgatccgtg cctgaagatc    6540
cgtgggttgg caaatattag agtcgttgat gcgtcaatta tgccgcactt ggtcgcgggt    6600
aacacaaacg ctccaactat tatgattgca gaaaatgcgg cagaaataat tatgcggaat    6660
cttgatgtgg aagcattaga ggctagcgct gagtttgctc gcgagggtgc agagctagag    6720
ttggcctggc gcgccctcga gggatcccac gtgctggtgc cgcgtggcag cgcggccgca    6780
ctggagcacc accaccacca ccaccaccac tgagatccgg ctgctaacaa agcccgaaag    6840
gaagctgagt tggctgctgc caccgctgag caataactag cataacccct tggggcctct    6900
aaacgggtct tgaggggttt tttgctgaaa ggaggaacta tatccggat               6949
```